US009604456B2

(12) United States Patent
Kobayashi

(10) Patent No.: US 9,604,456 B2
(45) Date of Patent: Mar. 28, 2017

(54) LIQUID EJECTION DEVICE ACTUATOR UNIT AND LIQUID EJECTION DEVICE HANDPIECE

(71) Applicant: SEIKO EPSON CORPORATION, Tokyo (JP)

(72) Inventor: Akio Kobayashi, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 15/077,744

(22) Filed: Mar. 22, 2016

(65) Prior Publication Data

US 2016/0279946 A1    Sep. 29, 2016

(30) Foreign Application Priority Data

Mar. 23, 2015    (JP) ................................. 2015-059272

(51) Int. Cl.
  *B41J 2/14*    (2006.01)
  *A61B 17/3203*    (2006.01)

(52) U.S. Cl.
  CPC ....... *B41J 2/14233* (2013.01); *A61B 17/3203* (2013.01)

(58) Field of Classification Search
  CPC ....... A61B 17/3203; A61B 2017/00473; B41J 2/14233; B41J 2/14274; B41J 2002/14241; B05C 11/1013
  See application file for complete search history.

(56) References Cited

U.S. PATENT DOCUMENTS 5,818,482 A * 10/1998 Ohta .................... B41J 2/14274
  347/40
6,305,791 B1 * 10/2001 Hotomi ................ B41J 2/14274
  347/70

(Continued)

FOREIGN PATENT DOCUMENTS

JP    H11-326363 A    11/1999
JP    2000-117992 A    4/2000

(Continued)

OTHER PUBLICATIONS

Extended European Search Report dated Sep. 2, 2016 as received in Application No. 16161357.5.

*Primary Examiner* — Anh T. N. Vo
(74) *Attorney, Agent, or Firm* — Maschoff Brennan

(57) ABSTRACT

A liquid ejection device actuator unit is fitted to a nozzle unit including a liquid chamber of which an inside volume is variable by deformation of a liquid chamber side diaphragm and an ejection tube which ejects a liquid from the liquid chamber. The liquid ejection device actuator unit includes a movable plate which comes into contact with the liquid chamber side diaphragm, a piezoelectric element which comes into contact with the movable plate at one end of the piezoelectric element in an expansion or contraction direction to deform the movable plate, and a support member which is adhered to the piezoelectric element at other end of the piezoelectric element in the expansion or contraction direction. At least one of a contact portion of the movable plate and the piezoelectric element and a contact portion of the piezoelectric element and the support member is adhered by a hard material containing adhesive in which a hard material with a larger elastic modulus than a hardened adhesive is mixed.

5 Claims, 11 Drawing Sheets

(56) References Cited

U.S. PATENT DOCUMENTS

| | | | |
|---|---|---|---|
| 7,901,374 B2* | 3/2011 | Seto | A61B 17/3203 604/131 |
| 2008/0086077 A1 | 4/2008 | Seto et al. | |
| 2013/0214058 A1* | 8/2013 | Kawakami | A61B 17/3203 239/154 |
| 2014/0134001 A1 | 5/2014 | Uchida et al. | |

FOREIGN PATENT DOCUMENTS

| | | |
|---|---|---|
| JP | 2002-240283 A | 8/2002 |
| JP | 2007-21911 A | 2/2007 |
| JP | 2010-59902 A | 3/2010 |
| JP | 2014-95353 A | 5/2014 |

\* cited by examiner

LIQUID EJECTION DEVICE ACTUATOR UNIT AND LIQUID EJECTION DEVICE HANDPIECE

BACKGROUND

1. Technical Field

The present invention relates to ejection of a liquid.

2. Related Art

Liquid ejection devices using stacked piezoelectric elements are known (see JP-A-2014-95353). The technology disclosed in JP-A-2014-95353 is as follows. That is, one end of a piezoelectric element is adhered to a movable plate. The movable plate is a plate referring to a collective of a top plate (piston) and a diaphragm. An end at the other end of the piezoelectric element is adhered to a bottom portion (support member). The diaphragm is adhered to a housing of which a circumferential portion accommodates the piezoelectric element and partitions a liquid chamber. The diaphragm varies the volume of the liquid chamber by driving the piezoelectric element.

In the case of the foregoing technology of the related art, the adhering of the piezoelectric element and the movable plate and the adhering of the piezoelectric element and the support member have not been examined in detail. For example, the fact that the adhering is realized by an adhesive or is realized by another method has not been disclosed. Such adhering has an influence not only on a variation in the volume of the liquid chamber by the piezoelectric element but also on pressure of the liquid to be ejected.

SUMMARY

An advantage of some aspects of the invention is that at least any of the foregoing adhering is appropriately realized using an adhesive in consideration of the technology of the related art.

The invention can be implemented as the following forms.

(1) An aspect of the invention provides a liquid ejection device actuator unit which is fitted to a liquid ejection device nozzle unit including a liquid chamber of which an inside volume is variable by deformation of a liquid chamber side diaphragm and an ejection tube which ejects a liquid from the liquid chamber. The liquid ejection device actuator unit includes: a movable plate which comes into contact with the liquid chamber side diaphragm; a piezoelectric element which comes into contact with the movable plate at one end of the piezoelectric element in an expansion or contraction direction to deform the movable plate; and a support member which comes into contact with the piezoelectric element at other end of the piezoelectric element in the expansion or contraction direction. At least one of a contact portion of the movable plate and the piezoelectric element and a contact portion of the piezoelectric element and the support member is adhered by a hard material containing adhesive in which a hard material with a larger elastic modulus than a hardened adhesive is mixed. According to the aspect of the invention, at least one of the adhering of the movable plate and the piezoelectric element and the adhering of the piezoelectric element and the support member can be appropriately realized. The hard material is mixed in the adhesive. Therefore, even when the piezoelectric element expands, a gap between the adhesion surfaces is rarely narrowed. As a result, it is possible to efficiently reduce the volume of the liquid chamber through the expansion of the piezoelectric element.

(2) In the aspect of the invention, the movable plate may include a piston and a piezoelectric element side diaphragm. Apart of the piezoelectric element side diaphragm may be fixed to a housing accommodating the piezoelectric element. The piston and the piezoelectric element side diaphragm may come into contact with each other. The piezoelectric element and the movable plate may be adhered by adhering the piezoelectric element and the piston. The liquid chamber side diaphragm may come into contact with the movable plate by bringing the liquid chamber side diaphragm into contact with the piezoelectric element side diaphragm. According to the aspect of the invention with this configuration, the movable plate can be formed in a division manner by the piston and the piezoelectric element side diaphragm.

(3) In the aspect of the invention, the piston and the piezoelectric element side diaphragm may be adhered by the hard material containing adhesive. According to the aspect of the invention with this configuration, when the piezoelectric element contracts, the following property of the piezoelectric element side diaphragm becomes better.

The invention can be implemented in other various forms. For example, while the movable plate is provided, the liquid chamber side diaphragm may not be provided. Additionally, a liquid ejection device handpiece including a liquid ejection device nozzle unit and the foregoing liquid ejection device actuator unit can be implemented or a liquid ejection device including the liquid ejection device handpiece and a liquid supply device can be implemented.

BRIEF DESCRIPTION OF THE DRAWINGS

The invention will be described with reference to the accompanying drawings, wherein like numbers reference like elements.

DESCRIPTION OF EXEMPLARY EMBODIMENTS

First, an ejection mechanism and a suction mechanism for a liquid will be described by describing an overall of a liquid ejection device 20 with reference to FIGS. 1 to 10.

Figure 1:
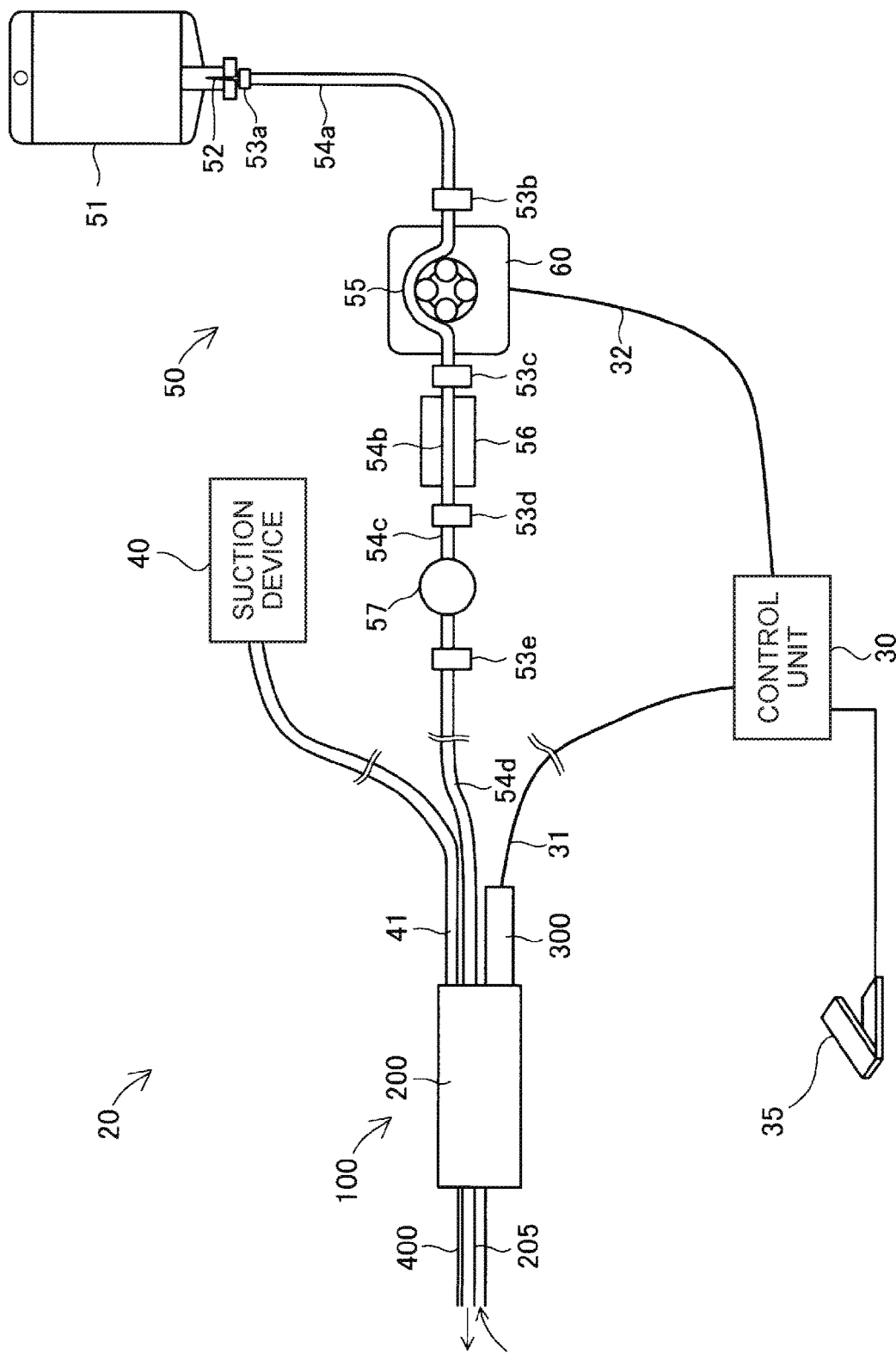
FIG. 1 is a diagram illustrating the schematic configuration of a liquid ejection device.

FIG. 1 schematically illustrates the configuration of the liquid ejection device 20. The liquid ejection device 20 is a medical apparatus used in a medical institution and has a function of excising a diseased part by ejecting a liquid to the diseased part.

The liquid ejection device 20 includes a control unit 30, an actuator cable 31, a pump cable 32, a foot switch 35, a suction device 40, a suction tube 41, and a liquid supply device 50, and a handpiece 100 (operation unit).

The liquid supply device 50 includes a water feed bag 51, a spike needle 52, a first connector 53a to a fifth connector 53e, a first water feed tube 54a to a fourth water feed tube 54d, a pump tube 55, a blockade detection mechanism 56, and a filter 57. The handpiece 100 includes a nozzle unit 200 and an actuator unit 300. The nozzle unit 200 includes an ejection tube 205 and a suction tube 400.

The water feed bag 51 is made of a transparent synthetic resin and is filled internally with a liquid (specifically, a physiological salt solution). In the present specification, a bag filled with a liquid other than water is also referred to as the water feed bag 51. The spike needle 52 is connected to the first water feed tube 54a via the first connector 53a. When the spike needle 52 is punctured into the water feed bag 51, the liquid with which the water feed bag 51 is filled can be supplied to the first water feed tube 54a.

The first water feed tube 54a is connected to the pump tube 55 via the second connector 53b. The pump tube 55 is connected to the second water feed tube 54b via the third connector 53c. In the tube pump 60, the pump tube 55 is interposed between a stator and a rotor. The tube pump 60 passes (thrusts) the pump tube 55 by rotating a plurality of rollers through rotation of an internal motor. Bypassing the pump tube 55, the liquid inside the pump tube 55 is sent from the side of the first water feed tube 54a to the side of the second water feed tube 54b.

The blockade detection mechanism 56 detects blockade inside the first water feed tube 54a to the fourth water feed tube 54d by measuring pressure inside the second water feed tube 54b.

The second water feed tube 54b is connected to the third water feed tube 54c via the fourth connector 53d. The filter 57 is connected to the third water feed tube 54c. The filter 57 captures foreign matters contained in the liquid.

The third water feed tube 54c is connected to the fourth water feed tube 54d via the fifth connector 53e. The fourth water feed tube 54d is connected to the handpiece 100. The liquid supplied to the handpiece 100 via the fourth water feed tube 54d is intermittently ejected from a nozzle 207 formed at the leading end of the ejection tube 205 through the driving of the actuator unit 300. By intermittently ejecting the liquid in this way, it is possible to ensure an excising capacity at a small flow rate.

The ejection tube 205 and the suction tube 400 are configured as double tubes in which the ejection tube 205 is an internal tube and the suction tube 400 is an external tube. The suction tube 41 is connected to the nozzle unit 200. The suction device 40 sucks the inside of the suction tube 400 via the suction tube 41. Through the suction, the liquid or excised pieces near the leading end of the suction tube 400 is sucked.

The control unit 30 controls the tube pump 60 and the actuator unit 300. Specifically, the control unit 30 transmits a drive signal via the actuator cable 31 and the pump cable 32 while the foot switch 35 is stepped. The drive signal transmitted via the actuator cable 31 drives the actuator unit 300. The drive signal transmitted via the pump cable 32 drives the tube pump 60. Accordingly, while a user steps the foot switch 35, the liquid is intermittently ejected. While the user does not step the foot switch 35, the ejection of the liquid is stopped.

Figure 2:
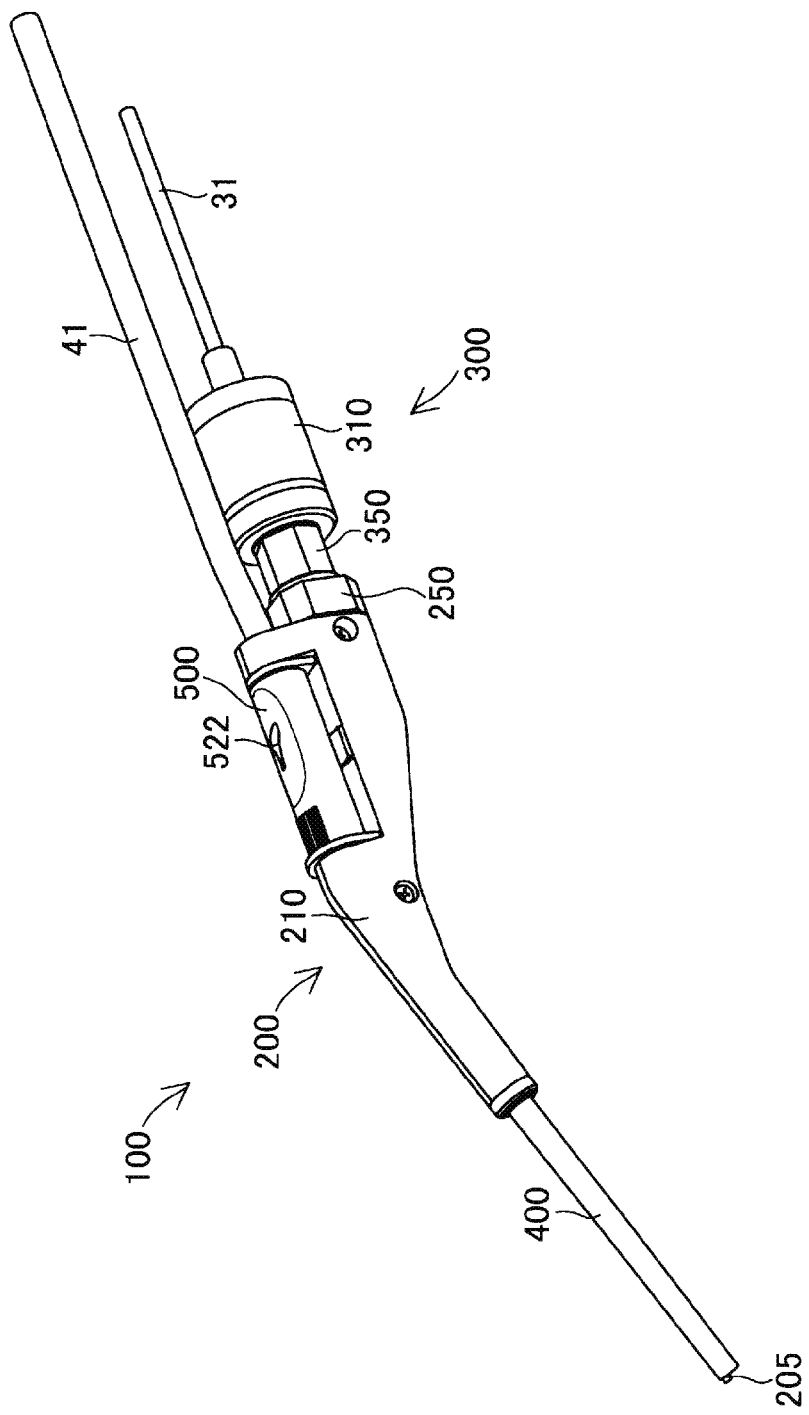
FIG. 2 is a perspective view illustrating a handpiece (fitted state).
Figure 3:
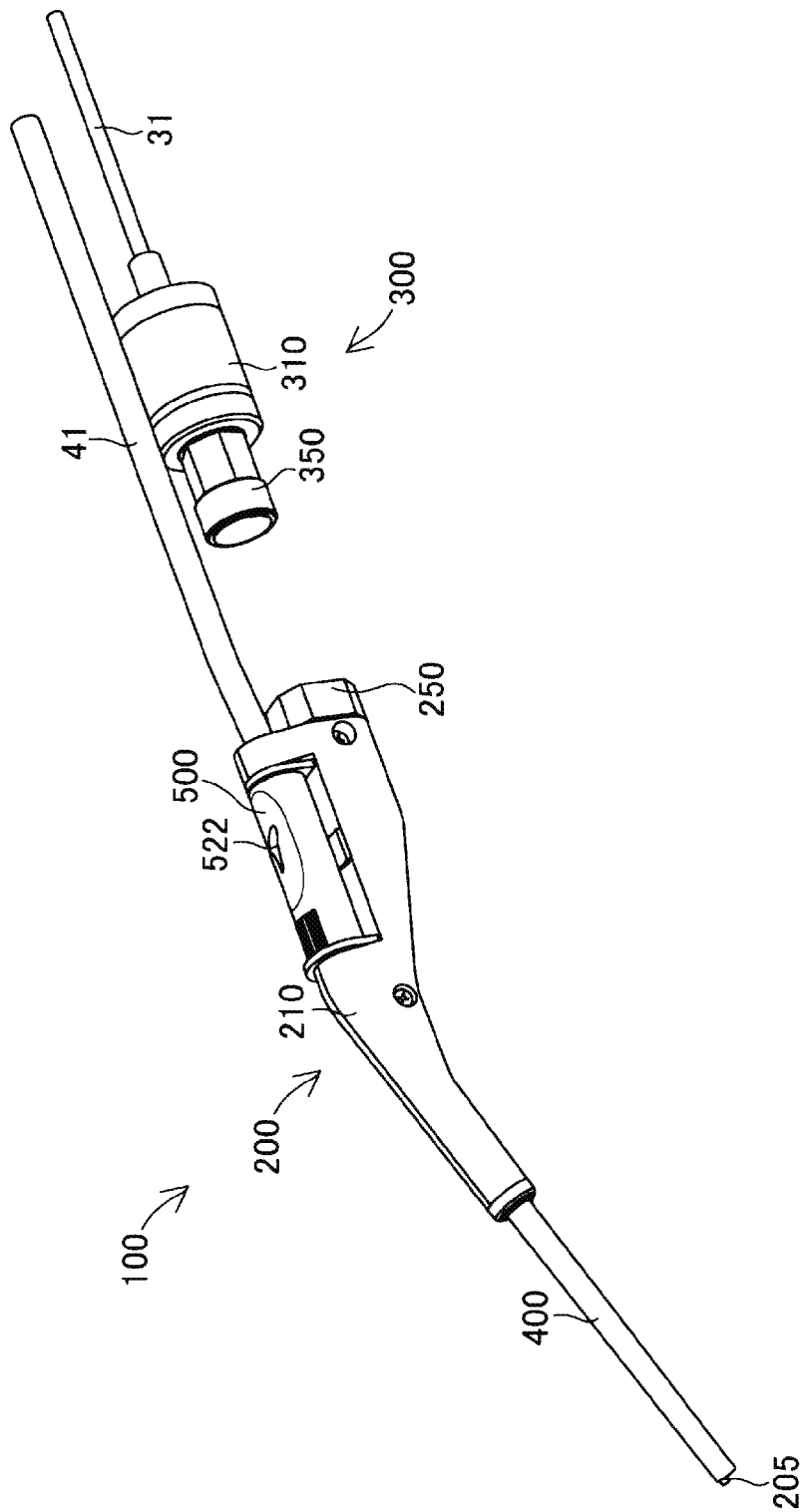
FIG. 3 is a perspective view illustrating the handpiece (separated state).

FIGS. 2 and 3 are perspective views illustrating the handpiece 100. FIG. 2 illustrates a state in which the actuator unit 300 is fitted to the nozzle unit 200 (hereinafter referred to as a "fitted state"). FIG. 3 illustrates a state in which the actuator unit 300 is separated from the nozzle unit 200 (hereinafter referred to as a "separated state").

The actuator unit 300 is configured to be detachably fitted to the nozzle unit 200. The actuator unit 300 is fitted to the nozzle unit 200 so that the actuator unit 300 and the nozzle unit 200 are integrated, and thus functions as the handpiece 100.

The liquid flows inside the nozzle unit 200, and thus the nozzle unit 200 is exchanged at each surgical operation. Of the constituent elements included in the liquid supply device 50, the constituent elements (the water feed bag 51, the first water feed tube 54a to the fourth water feed tube 54d, the pump tube 55, and the like) in which the liquid flows are exchanged at each surgical operation. Since the actuator unit 300 does not come into contact with the liquid, the actuator unit 300 can be used in a plurality of surgical operations by performing a sterilization treatment or a cleaning treatment.

The nozzle unit 200 includes a handpiece case 210, a joint portion 250, and a suction force adjustment mechanism 500 in addition to the ejection tube 205 and the suction tube 400 described above. The handpiece case 210 functions as a grip held by the user and has a function to maintain a channel internally. The channel is a channel along which the liquid to be ejected and the liquid to be sucked flow, as described above.

The suction force adjustment mechanism 500 is formed in the handpiece 100 and has a hole 522. When an open area of the hole 522 is changed, a suction force by the suction tube 400 is also changed (which will be described in detail with reference to FIG. 5). The joint portion 250 is a portion for detaching and fitting the actuator unit 300 from and to the nozzle unit 200.

The actuator unit 300 includes a connection portion 310 and a driving portion 350. The connection portion 310 mechanically and electrically connect the actuator cable 31 to the driving portion 350. The driving unit 350 generates a driving force to intermittently eject the liquid.

Figure 4:
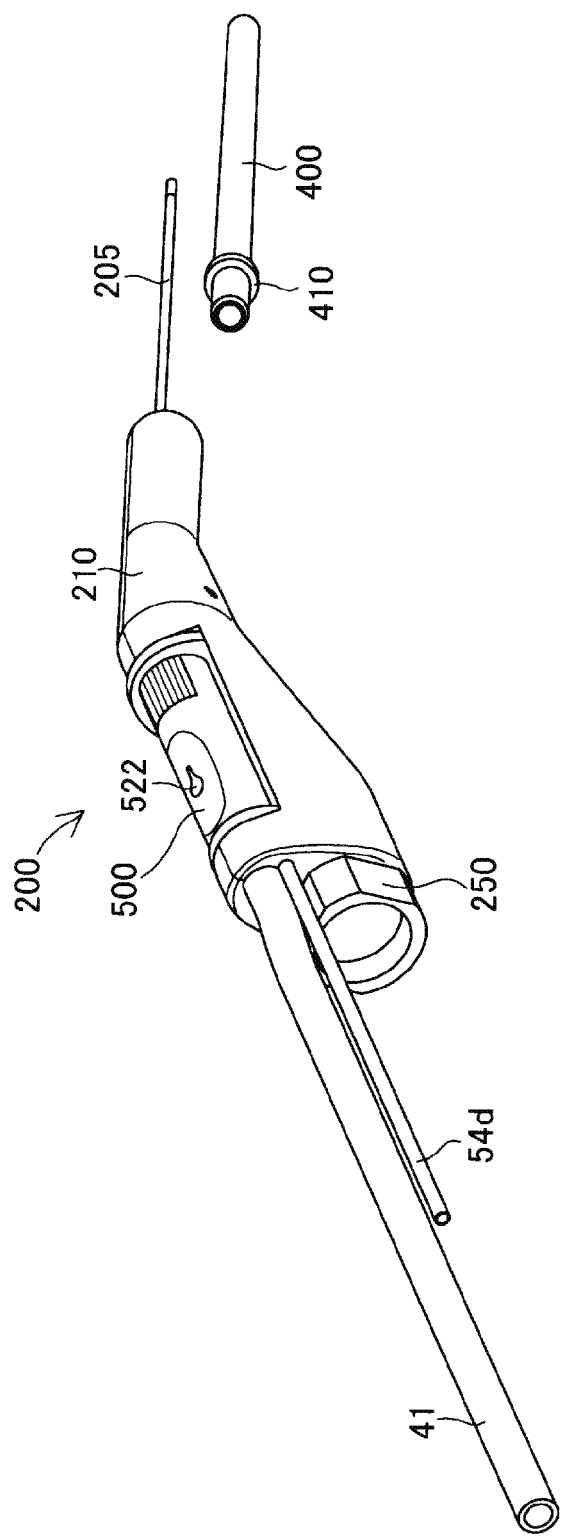
FIG. 4 is a perspective view illustrating a nozzle unit.

FIG. 4 is a perspective view illustrating the nozzle unit 200. FIG. 4 illustrates a state in which the suction tube 400 is detached from the handpiece case 210. The handpiece 100 may be used in the state in which the suction tube 400 is detached. In the state in which the suction tube 400 is detached, no suction can be performed using the suction tube 400, but the liquid can be ejected from the ejection tube 205.

The suction tube 400 includes a convex portion 410. The convex portion 410 is a portion that fits the suction tube 400 to the handpiece case 210.

As illustrated with reference to FIG. 1, the fourth water feed tube 54d is connected to the handpiece case 210. In FIGS. 2 and 3, the fourth water feed tube 54d is not illustrated due to visual perspective.

Figure 5:
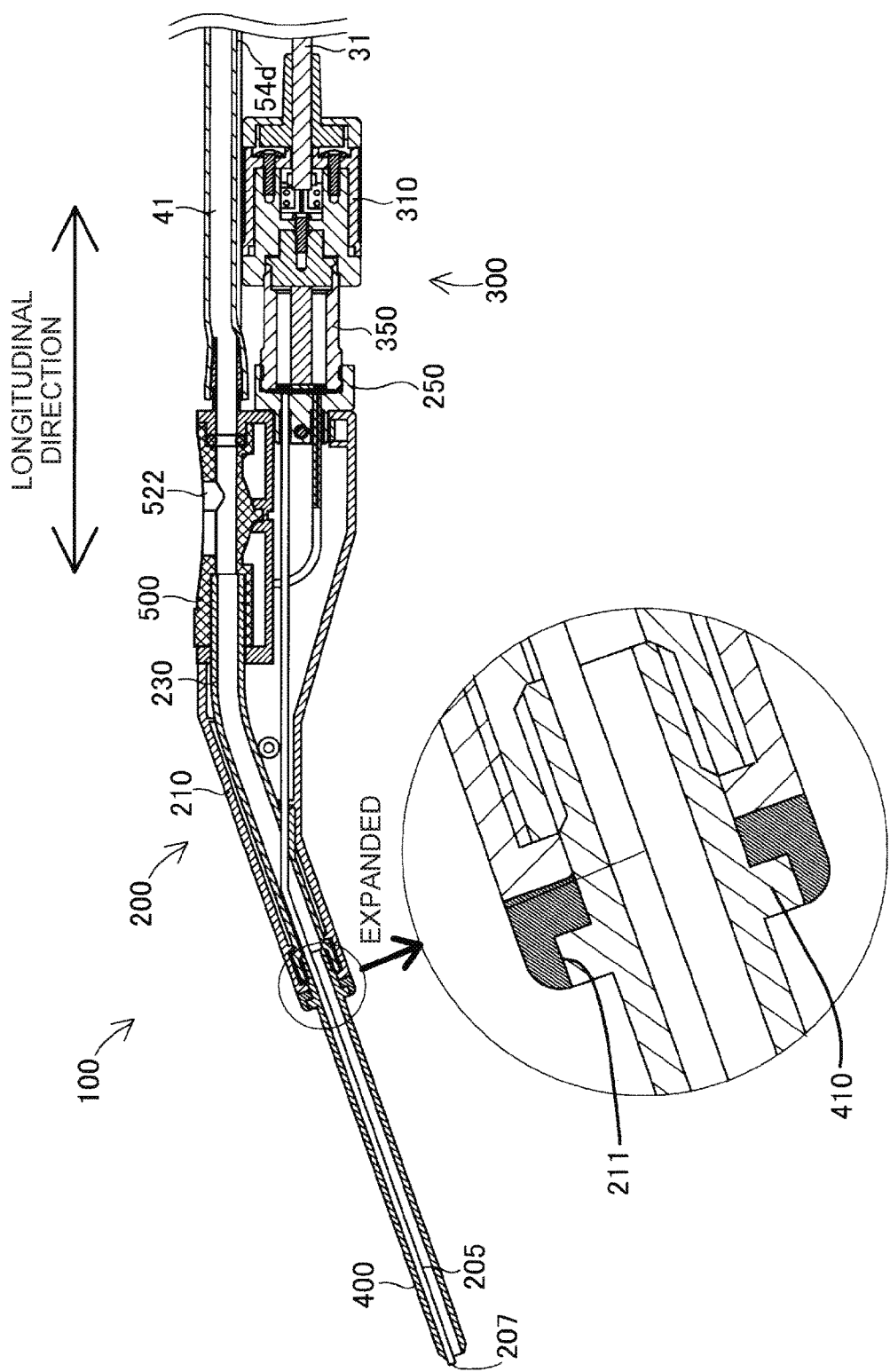
FIG. 5 is a sectional view illustrating the handpiece.

FIG. 5 is a sectional view illustrating the handpiece 100. The fourth water feed tube 54d is bent in a U shape inside the handpiece case 210 to be connected to an inlet channel 241. The inlet channel 241 communicates with the ejection tube 205 via a liquid chamber 240 (see FIGS. 8 and 9).

The channel diameter of the inlet channel 241 is less than the channel diameter of the ejection tube 205. Therefore, even when pressure varies inside the liquid chamber 240

(which will be described below), the liquid inside the liquid chamber 240 is prevented from flow backward into the inlet channel 241.

The handpiece case 210 includes a concave portion 211 at the leading end. The fitting of the suction tube 400 is realized by engaging the convex portion 410 with the concave portion 211. The fitted suction tube 400 communicates with a suction channel portion 230. The suction channel portion 230 is connected to the suction tube 41 via the suction force adjustment mechanism 500.

The user can adjust a suction force by the suction tube 400 using the hole 522. Specifically, when an open area of the hole 522 is small, the flow rate of the air flowing from the hole 522 is small. Therefore, the flow rate of a fluid (the air, the liquid, or the like) sucked via the suction tube 400 increases. That is, the suction force by the suction tube 400 increases. In contrast, when the open area of the hole 522 is large, the flow rate of the air flowing from the hole 522 is large. Therefore, the suction force by the suction tube 400 decreases. Normally, the user realizes adjustment of the open area of the hole 522 by adjusting the area of the hole 522 blocked by his or her thumb. When the hole 522 is not covered at all, the shape of the hole 522 is designed so that the suction force by the suction tube 400 is minute or the suction force does not work. In the embodiment, the flow channel area of the suction tube 400 is greater than the open area of the hole 522. However, by causing the length of the suction tube 400 to be greater than the length of the hole 522, channel resistance of the suction tube 400 is configured to be greater than channel resistance of the hole 522. In this way, when the hole 522 is not covered at all, the suction force by the suction tube 400 can be minute.

As illustrated in FIG. 5, the longitudinal direction of the handpiece case 210 is defined. The longitudinal direction is a direction included in the cross section illustrated FIG. 5 and a horizontal direction at the time of a predetermined posture. The predetermined posture is a posture at which the user holds the handpiece 100 with his or her hand of which the palm is oriented upward. The longitudinal direction according to the embodiment is identical to a channel direction of the suction channel portion 230. The channel direction of the suction channel portion 230 is a direction of a flow inside the suction channel portion 230 in a portion of the suction channel portion 230 coming into contact with the suction force adjustment mechanism 500.

Figure 6:
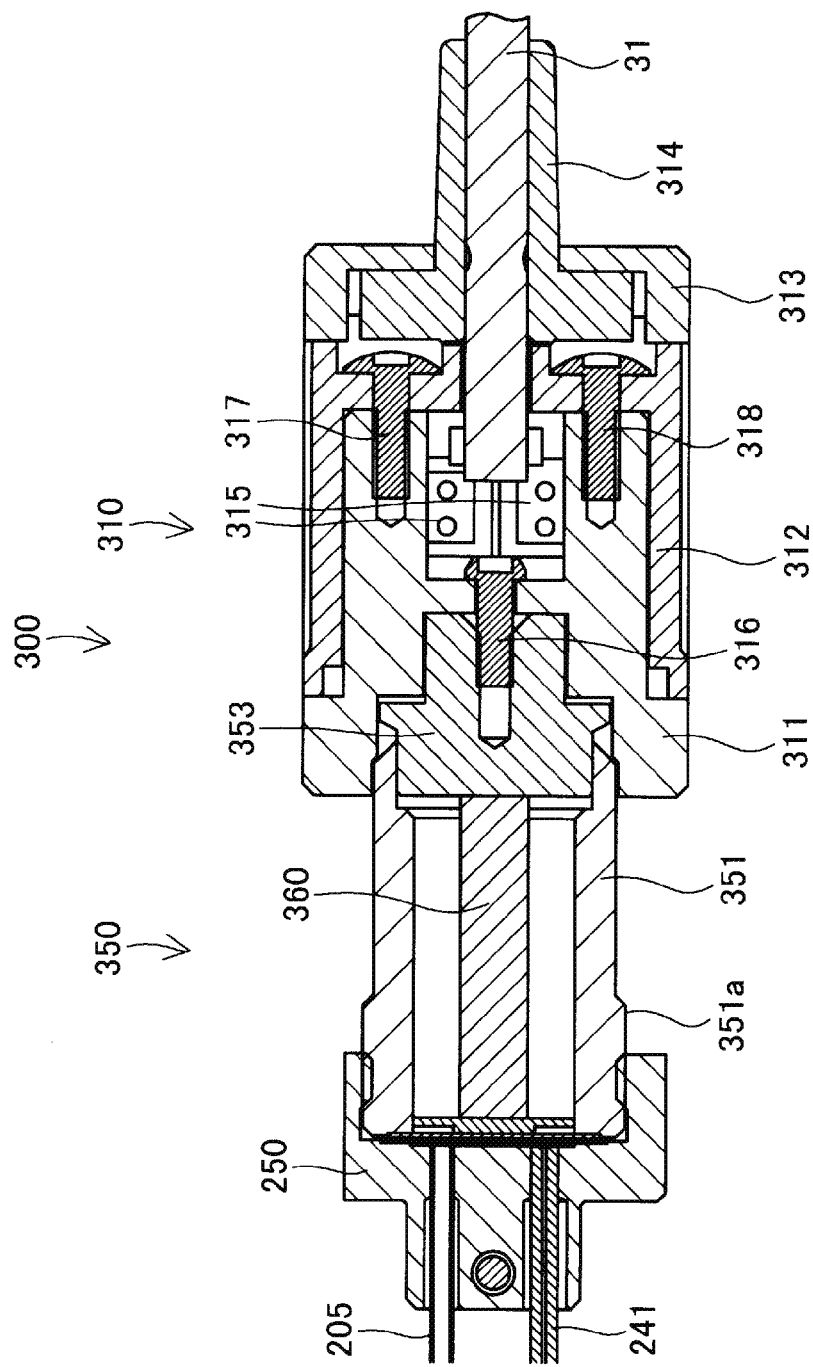
FIG. 6 is an expanded sectional view illustrating a joint portion and an actuator unit (fitted state).
Figure 7:
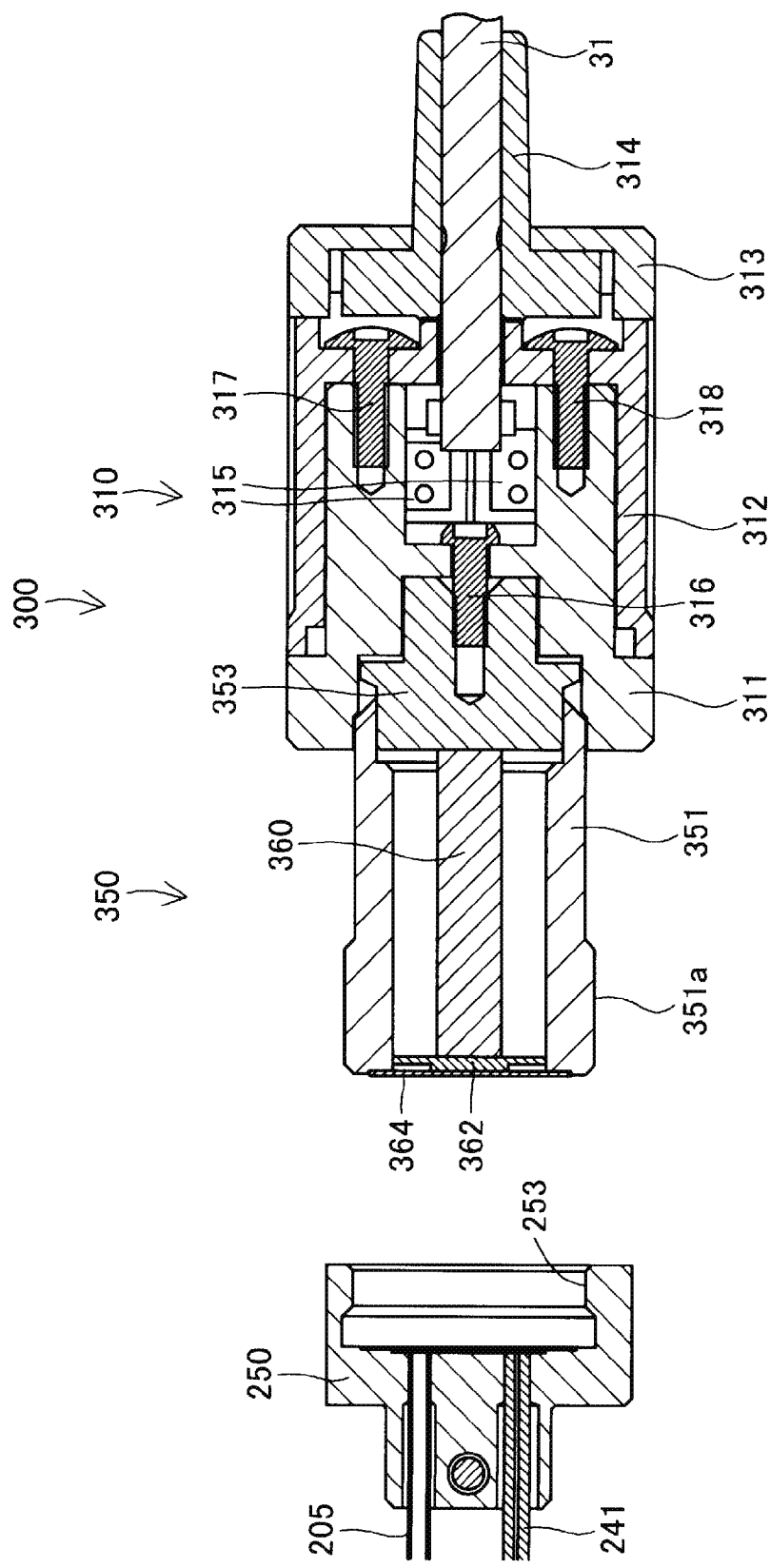
FIG. 7 is an expanded sectional view illustrating the joint portion and the actuator unit (separated state).

FIGS. 6 and 7 are expanded sectional views illustrating the vicinities of the joint portion 250 and the actuator unit 300. FIG. 6 illustrates a fitted state. FIG. 7 illustrates a separated state.

The driving portion 350 includes a housing 351, a support member 353, a piezoelectric element 360, and a movable plate 361. The housing 351 is a cylindrical member. The movable plate 361 includes a piston 362 and a driving side diaphragm 364.

The piezoelectric element 360 is a stacked piezoelectric element. The piezoelectric element 360 is disposed inside the housing 351 so that an expansion or contraction direction is parallel to the longitudinal direction of the housing 351. The piezoelectric element 360 according to the embodiment has a substantially right quadrangular prism shape with four sides of 3.5 mm and a height of 18 mm.

The support member 353 is fixed to one end of the housing 351. The piezoelectric element 360 is fixed to the support member 353 by an adhesive.

The material of the driving side diaphragm 364 is metal, specifically is stainless steel, and more specifically is SUS304 or SUS316L. The driving side diaphragm 364 has a thick form (for example, 300 μm) to perform preload (which will be described below) of the piezoelectric element 360. The piezoelectric element 360 is made of metal and the thick form. Therefore, when the piezoelectric element 360 is pushed by the piston 362, the piezoelectric element 360 is bent smoothly. Therefore, in the fitted state, a liquid chamber side diaphragm 260 can also be deformed smoothly.

The driving side diaphragm 364 is disposed to cover the other end of the housing 351 to be fixed to the housing 351 by welding.

The piston 362 is fixed to one end of the piezoelectric element 360 by an adhesive and is disposed to come into contact with the driving side diaphragm 364. The piston 362 has a shape in which columns with different diameters are stacked concentrically. The column with a small diameter comes into contact with the driving side diaphragm 364. Therefore, the end side of the driving side diaphragm 364 is not pushed and a large force is configured not to be applied to the welded portion. The piston 362 and the driving side diaphragm 364 merely come into contact with each other without being fixed by an adhesive or the like.

A male screw 351*a* is formed on the outer circumference of the housing 351. Transition from the separated state to the fitted state is realized by tightening the male screw 351*a* to a female screw 253 formed in the joint portion 250.

The connection portion 310 includes a first case 311, a second case 312, a third case 313, a hold member 314, metal plates 315, a first screw 316, a second screw 317, and a third screw 318. The metal plate 315 can also be restated as a relay substrate 315.

The first case 311 is fixed to the support member 353 by the first screw 316. The second case 312 is fixed to the first case 311 by the second screw 317 and the third screw 318. Two metal plates 315 are inserted (accommodated) inside the first case 311.

The hold member 314 is fastened to the vicinity of an end of the actuator cable 31 to be fixed. The third case 313 is a member which connects the second case 312 to the hold member 314. The third case 313 is locked in a portion in which the outer diameter of the hold member 314 is swollen, to be fixed to the second case 312.

In the foregoing fixed state, the actuator cable 31 is connected to be conductive with the two metal plates 315. The metal plates 315 are connected to positive and negative electrodes of the piezoelectric element 360 by wirings (not illustrated).

The piezoelectric element 360 are extracted or contracted according to a drive signal input via the actuator cable 31, the metal plates 315, and the wirings. When the piezoelectric element 360 is extracted or contracted, the piston 362 is vibrated in the longitudinal direction of the piezoelectric element 360. When the piston 362 is vibrated, the driving side diaphragm 364 follows the vibration to be deformed.

The piezoelectric element 360 is assembled in a preloaded state to appropriately perform the expansion or contraction. The preloaded state is a state in which the piezoelectric element 360 is pushed against the driving side diaphragm 364 and the piezoelectric element 360 is compressed in the expansion or contraction direction. A load of the preload is in the range of 10% to 50% of a maximum generation force of the piezoelectric element 360 and is specifically in the range of 40 N to 200 N. Therefore, even when no drive signal is input to the piezoelectric element 360, the driving side diaphragm 364 receives a force from the piezoelectric element 360 via the piston 362. The reason why the driving side diaphragm 364 is made of metal and is formed to be thicker than the liquid chamber side diaphragm 260 is to maintain the preload.

The driving side diaphragm 364 is deformed in the above-described manner. Therefore, even when the driving side diaphragm 364 is not attached to the piston 362, the driving side diaphragm 364 follows the contraction of the piezoelectric element 360 to be deformed.

Figure 8:
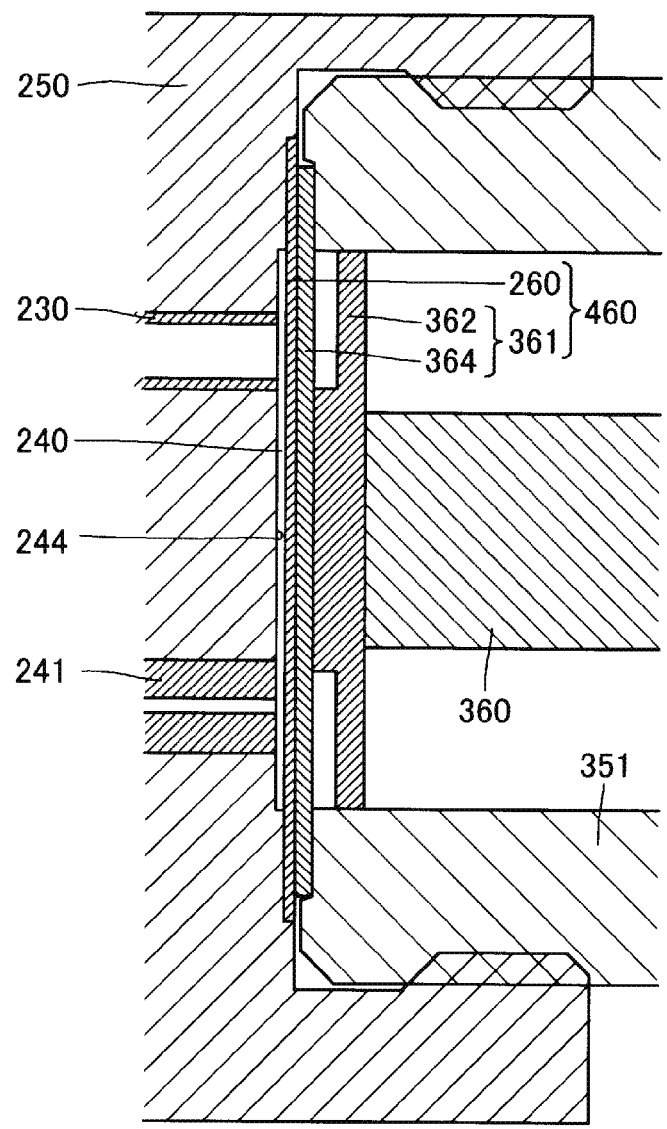
FIG. 8 is an expanded sectional view of the vicinity of a liquid chamber (fitted state).
Figure 9:
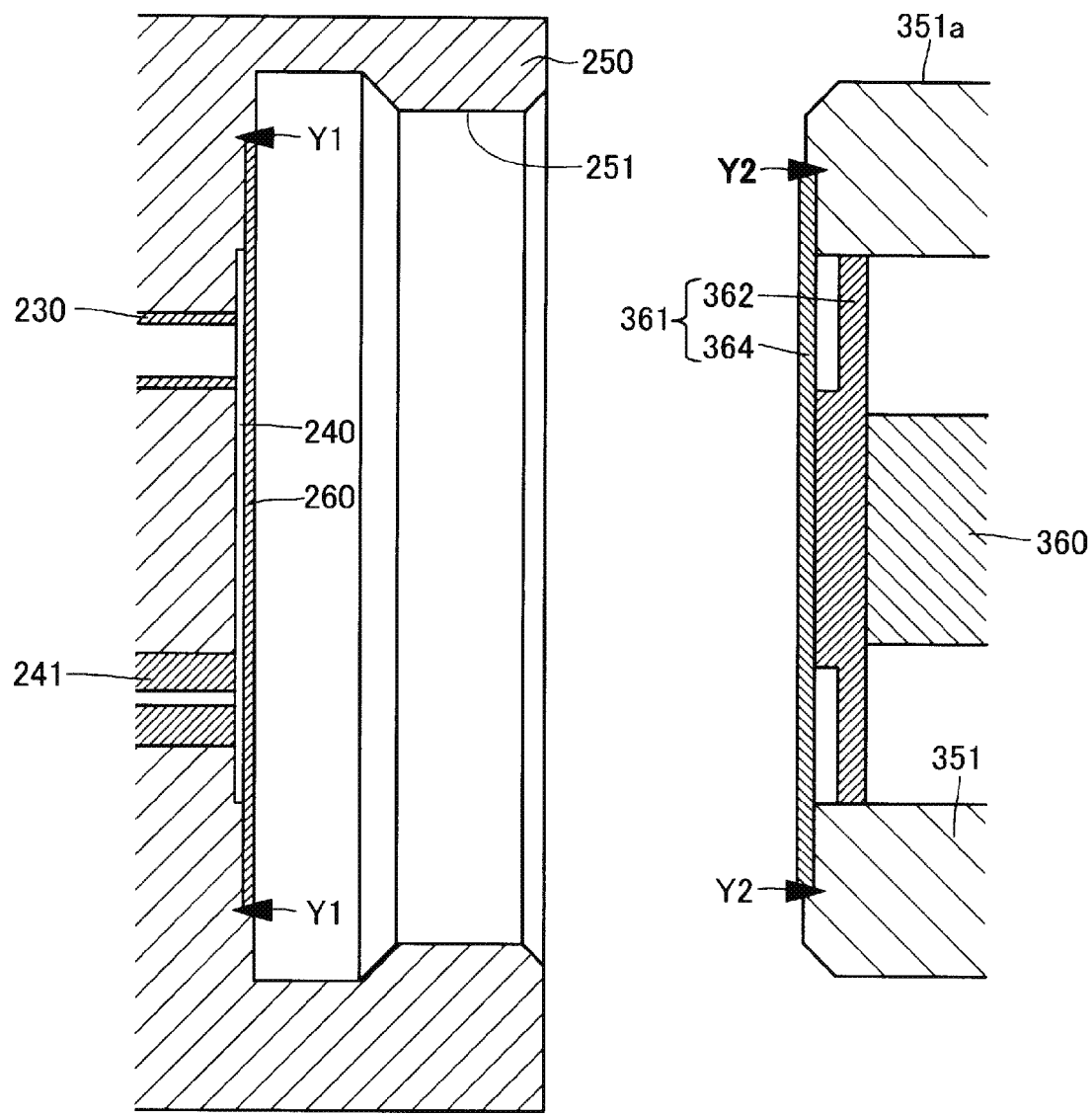
FIG. 9 is an expanded sectional view of the vicinity of the liquid chamber (separated state).

FIGS. 8 and 9 are expanded sectional view illustrating the vicinity of the liquid chamber 240. FIG. 8 illustrates a fitted state. FIG. 9 illustrates a separated state.

The liquid chamber 240 is formed inside the joint portion 250. The liquid chamber 240 is formed in a hollow 244 by covering the liquid chamber side diaphragm 260. The hollow 244 is a portion hollowed in a thin circular shape in the joint portion 250. The liquid chamber side diaphragm 260 is formed to be thinner than the driving side diaphragm 364 (for example, 50 µm to 100 µm) so that the liquid chamber side diaphragm 260 is easily deformed according to the expansion or contraction of the piezoelectric element 360. The diameter of the liquid chamber side diaphragm 260 is in the range of 13 mm to 15 mm. The liquid chamber side diaphragm 260 is fixed to the joint portion 250 by welding. The welded positions are illustrated as welds Y1 in FIG. 9. The material of the liquid chamber side diaphragm 260 is metal, specifically is stainless steel, and more specifically is SUS304 or SUS316L.

As illustrated in FIG. 8, the liquid chamber side diaphragm 260 and the driving side diaphragm 364 come into contact with each other in the fitted state. Therefore, as described above, when the driving side diaphragm 364 is deformed, the liquid chamber side diaphragm 260 is also deformed similarly.

When the driving side diaphragm 364 is deformed, the volume of the liquid chamber 240 varies. Due to this variation, the pressure of the liquid with which the liquid chamber 240 is filled varies. When the pressure inside the liquid chamber 240 decreases, the liquid flows into the liquid chamber 240 from the inlet channel 241. When the pressure inside the liquid chamber 240 increases, the liquid flows out to the ejection tube 205 from the liquid chamber 240. The liquid flowing out to the ejection tube 205 is ejected from the leading end of the ejection tube 205. Since the pressure inside the liquid chamber 240 intermittently increases, the liquid is intermittently ejected from the ejection tube 205.

In this way, the liquid chamber side diaphragm 260 and the driving side diaphragm 364 are integrated to be deformed. That is, the liquid chamber side diaphragm 260 and the movable plate 361 are integrated to be deformed. Reference numeral 460 illustrated in FIG. 8 denotes a combined diaphragm 460 in which the liquid chamber side diaphragm 260 and the movable plate 361 integrated to be deformed are combined. The combined diaphragm 460 can be comprehended as a single diaphragm in the fitted state.

Figure 10:
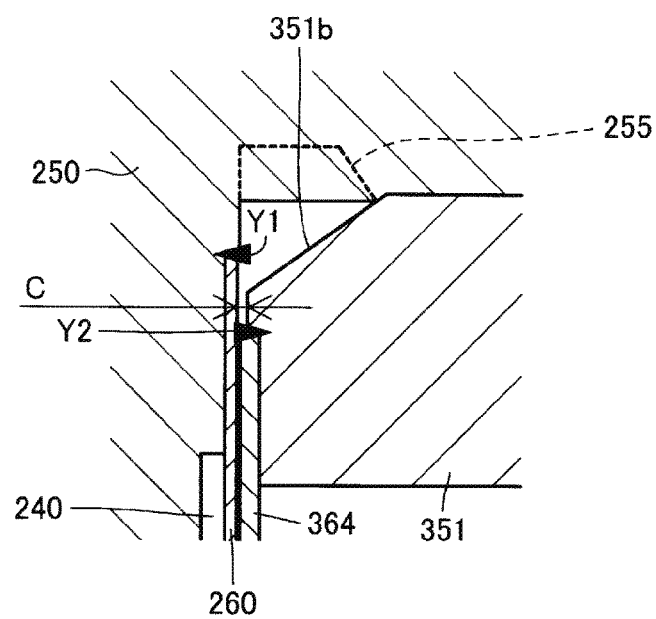
FIG. 10 is a diagram illustrating welding of a liquid chamber side diaphragm and a piezoelectric element side diaphragm.

FIG. 10 is a diagram illustrating welding of the liquid chamber side diaphragm 260 and the driving side diaphragm 364. In the housing 351, a chamfered portion 351b is formed, as illustrated in FIG. 10. The chamfered portion 351b is formed so that the welds Y1 fixing the liquid chamber side diaphragm 260 and the housing 351 are not interfered with each other.

As illustrated in FIG. 10, the leading end of the housing 351 is recessed by a size C than the leading end of the driving side diaphragm 364. As a result, in the fitted state, a clearance occurs between the liquid chamber side diaphragm 260 and the housing 351. By performing welding so that a welding mark of a weld Y2 fixing the driving side diaphragm 364 is located at the clearance, it is possible to avoid interference between the weld Y2 and the liquid chamber side diaphragm 260.

Reference numeral 255 illustrated in FIG. 10 denotes a relief portion 255 in another form. In the embodiment, as illustrated in FIGS. 8 and 9 and the like, the relief portion 255 is not formed. The relief portion 255 is a portion in which a wall is recessed inward in the inner circumference of the joint portion 250. By forming the relief portion 255, the female screw 253 is easily processed.

Hereinafter, adhesion of the piezoelectric element 360 will be described.

Figure 11:
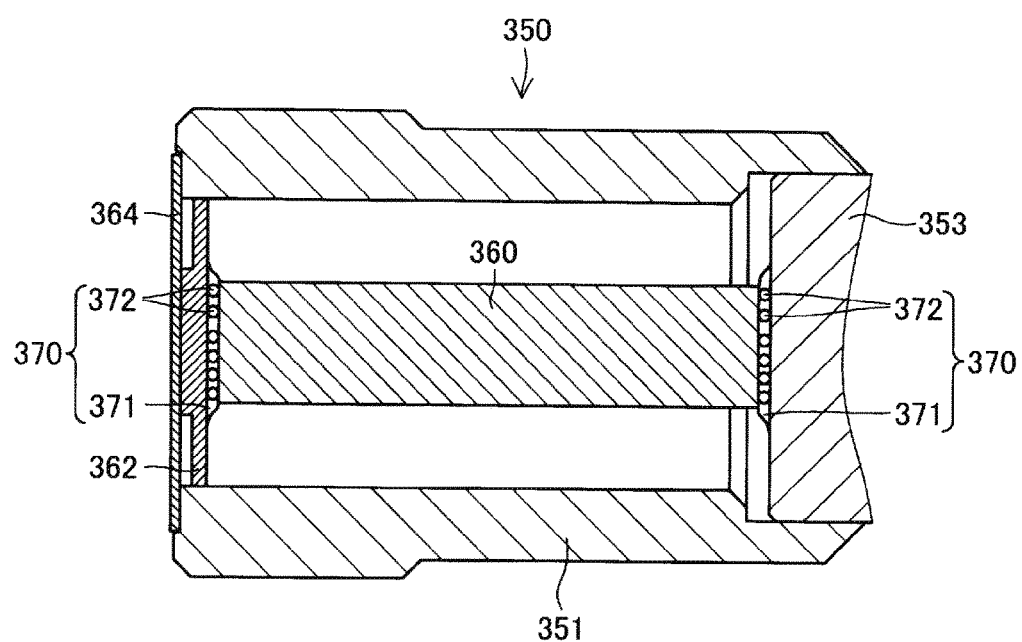
FIG. 11 is a sectional view illustrating a driving portion.

FIG. 11 is a sectional view illustrating the driving portion 350. The piezoelectric element 360 is fixed to the support member 353 and the piston 362 by an adhesive, as described above. The adhesive is a hard material containing adhesive 370 illustrated in FIG. 11. The hard material containing adhesive 370 is an adhesive in which many hard materials 372 are mixed in an adhesive 371. A mixing ratio (mass ratio) of the adhesive 371 and the hard materials 372 is 10:1.

The adhesive 371 according to the embodiment is an epoxy-based adhesive. A storage elastic modulus after hardening of the adhesive 371 is 2.77 GPa at 25° C.

The hard material 372 according to the embodiment is made of silica (quartz glass), has an elastic modulus of 72 GPa, and has a substantially spherical shape of a diameter of 10 µm. A variation in the diameters of the hard materials 372 is small to the extent that the diameters of the hard materials are substantially uniform. In the embodiment, fine spherical particles manufactured by JGC Catalysts and Chemicals Ltd. were used as the hard materials 372.

When the support member 353 and the piezoelectric element 360 are adhered and the piezoelectric element 360 and the piston 362 are adhered, the adhesive 371 is hardened while mutually pressing the adhesion surfaces. The adhering of the support member 353 and the piezoelectric element 360 and the adhering of the piezoelectric element 360 and the piston 362 may be simultaneously performed or separately performed. The adhesion surfaces of the support member 353, the piezoelectric element 360, and the piston 362 are all flat surfaces.

The hard materials 372 have the spherical shape, as described above. Therefore, when the adhesion surfaces are mutually pressed, the adhesion surfaces are arranged in one layer and the adhesion surfaces substantially come into contact with each other. Therefore, the gaps between the adhesion surfaces are substantially the same as the diameters of the hard materials 372. The "adhesion surface substantially come into contact with each other" means that the thickness of the adhesive 371 present between the hard materials 372 and the adhesion surfaces is minute. Therefore, in portions in which the hard materials 372 are not present, the thickness of the adhesive 371 is ensured by the diameters of the hard materials 372, and thus an adhesive force is satisfactory.

Since the diameters of the hard materials 372 are substantially uniform, the adhesion surfaces are substantially parallel to each other. As a result, the support member 353, the piezoelectric element 360, and the piston 362 can be arranged substantially straightly.

The hard material 372 has a higher elastic modulus than the adhesive 371 and the adhesion surfaces are substantially come into contact with each other, as described above. Therefore, when the piezoelectric element 360 extends, most of a compressive force loaded to the adhesive 370 is loaded to the hard materials 372.

The hard material 372 has the high elastic modulus. Therefore, even when the compressive force is received due to the extension of the piezoelectric element 360, the hard material 372 is not deformed much. As a result, the extension of the piezoelectric element 360 efficiently deforms the liquid chamber side diaphragm 260 and the piezoelectric element side diaphragm 364 and further efficiently reduces the volume of the liquid chamber 240. As a result, the excising performance by the intermittent ejection is ensured.

The invention is not limited to the embodiments, the examples, and the modification examples of the present specification, but can be realized in various configurations in the scope of the invention without departing from the gist of the invention. For example, technical features of the embodiments, the examples, and the modification examples corresponding to technical features of the aspects described in Summary of the invention can be appropriately replaced or combined to resolve some or all of the above-described problems or achieve some or all of the above-described advantages. When the technical features are not described as requisites in the present specification, the technical features can be appropriately cancelled. For example, the followings can be exemplified.

Figure 12:
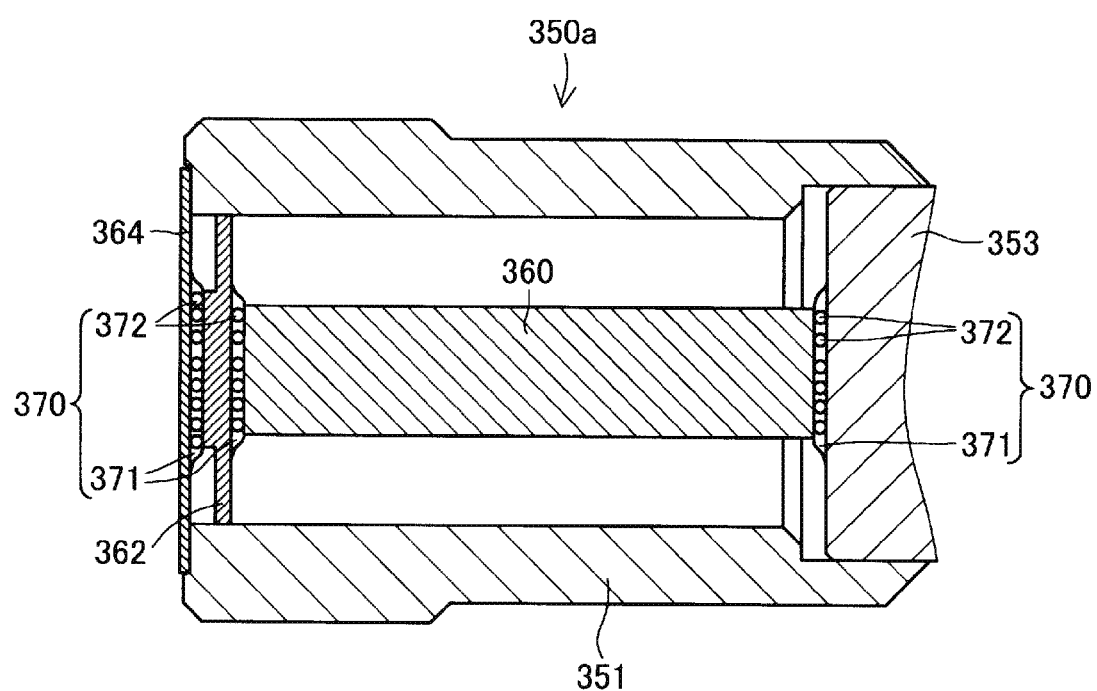
FIG. 12 is a sectional view illustrating a driving portion (modification example).

FIG. 12 is a sectional view illustrating a driving portion 350a. The driving portion 350a is used instead of the driving portion 350 described in the embodiment. The driving portion 350a is different from the driving portion 350 in that the piston 362 and the piezoelectric element side diaphragm 364 are adhered by the adhesive 370. Further, the driving portion 350a is different from the driving portion 350 in that the piezoelectric element 360 can be assembled without being preloaded. Even in such a configuration, the piezoelectric element side diaphragm 364 has a good following property for contraction of the piezoelectric element 360.

Any material can be used as the hard material as long as the material has a higher elastic modulus than the hardened adhesive. For example, metal such as iron or aluminum may be used.

The adhering by the hard material containing adhesive may be either adhering of the movable plate and the piezoelectric element or the adhering of the piezoelectric element and the support member. The adhering not using the hard material containing adhesive may be realized by an adhesive containing no hard material or the adhering may not be realized.

A structure for positioning the piezoelectric element to the adhesive surface of the support member before the adhesion may be provided. For example, a circular hollow may be formed as this structure. The diameter of the circle is assumed to be a value slightly greater than a diagonal line of an end surface of the piezoelectric element.

The piston may have a columnar shape. That is, the piston may be formed as a column with a single diameter.

The piston may not be formed. In this case, the movable plate is configured by only the piezoelectric element side diaphragm.

The number of diaphragms may be one or three or more. When the number of diaphragms is one, the liquid chamber side diaphragm may be disused or the driving side diaphragm may be disused. For example, when the liquid chamber side diaphragm is disused, the liquid chamber may not be formed in the separated state and may be formed in the fitted state. Specifically, when the separated state transitions to the fitted state, the driving side diaphragm is hung over the hollow so that a liquid chamber may be formed as a space partitioned by the driving side diaphragm and the hollow.

Alternatively, when the number of diaphragms is one, the nozzle unit and the actuator unit may be configured to be integrated. The integrated nozzle unit and actuator unit may be comprehended as an actuator unit or may be comprehended as a handpiece.

When the number of diaphragms is one, a combined diaphragm is configured by the diaphragm and the piston. As another form, when the piston is not present, one diaphragm corresponds to a combined diaphragm in the embodiment.

The piezoelectric element is preloaded, and the piston and the piezoelectric element side diaphragm may be adhered by an adhesive.

The liquid to be ejected may be pure water or a liquid medicine.

The liquid ejection device may be used for a device other than a medical apparatus.

For example, the liquid ejection device may be used for a cleaning device which removes dirt using an ejected liquid or may be used for a drawing device which draws a line or the like using an ejected liquid.

In the embodiment, the configuration in which the piezoelectric element is used as an actuator has been adopted, but a configuration in which a liquid is ejected using an optical maser may be adopted or a configuration in which a liquid is ejected by pressurizing the liquid by a pump or the like may be adopted. The configuration in which a liquid is ejected using an optical maser is a configuration in which an optical maser is emitted to a liquid to generate bubbles and a pressure increase of the liquid occurring by the generation of the bubbles is used.

In the embodiment, the configuration in which the liquid is intermittently ejected has been adopted, but a configuration having a function of continuously ejecting a liquid may be adopted. For example, a configuration in which intermittent ejection and continuous ejection may be distinguished to be used may be adopted. To perform the continuous ejection using the hardware configuration of the embodiment, only the tube pump may be driven when the driving of the actuator stops or deteriorates. In the case of this configuration, the intermittent ejection may be performed for excising and the continuous ejection may be performed for cleaning.

Alternatively, a configuration in which only continuous ejection can be performed may be adopted. In the case of this configuration, excising may be performed through the continuous ejection.

The entire disclosure of Japanese Patent Application No. 2015-059272 filed Mar. 23, 2015 is expressly incorporated by reference herein.

What is claimed is:

1. A liquid ejection device actuator unit which is fitted to a liquid ejection device nozzle unit including a liquid chamber of which an inside volume is variable by deformation of a liquid chamber side diaphragm and an ejection tube which ejects a liquid from the liquid chamber, the liquid ejection device actuator unit comprising:
   a movable plate which comes into contact with the liquid chamber side diaphragm;
   a piezoelectric element which comes into contact with the movable plate at one end of the piezoelectric element in an expansion or contraction direction to deform the movable plate; and
   a support member which comes into contact with the piezoelectric element at other end of the piezoelectric element in the expansion or contraction direction,
   wherein at least one of a contact portion of the movable plate and the piezoelectric element and a contact portion of the piezoelectric element and the support member is adhered by a hard material containing adhesive in which a hard material with a larger elastic modulus than a hardened adhesive is mixed.

2. The liquid ejection device actuator unit according to claim 1,
wherein the movable plate includes a piston and a piezoelectric element side diaphragm,
wherein a part of the piezoelectric element side diaphragm is fixed to a housing accommodating the piezoelectric element,
wherein the piston and the piezoelectric element side diaphragm come into contact with each other,
wherein the piezoelectric element and the movable plate are adhered by adhering the piezoelectric element and the piston, and
wherein the liquid chamber side diaphragm comes into contact with the movable plate by bringing the liquid chamber side diaphragm into contact with the piezoelectric element side diaphragm.

3. The liquid ejection device actuator unit according to claim 2,
wherein the piston and the piezoelectric element side diaphragm are adhered by the hard material containing adhesive.

4. A liquid ejection device handpiece comprising:
a liquid chamber of which an inside volume is variable by deformation of a diaphragm;
a piezoelectric element which comes into contact with the diaphragm at one end of the piezoelectric element in an expansion or contraction direction to deform the diaphragm; and
a support member which comes into contact with the piezoelectric element at other end of the piezoelectric element in the expansion or contraction direction; and
an ejection tube which ejects a liquid supplied to the liquid chamber from the liquid chamber,
wherein at least one of a contact portion of the diaphragm and the piezoelectric element and a contact portion of the piezoelectric element and the support member is adhered by a hard material containing adhesive in which a hard material with a larger elastic modulus than a hardened adhesive is mixed.

5. A liquid ejection device actuator unit fitted to a liquid ejection device nozzle unit including an ejection tube which ejects a liquid, the liquid ejection device actuator unit comprising:
a movable plate which forms a liquid chamber of which an internal volume is variable when the liquid ejection device actuator unit is fitted to the liquid ejection device nozzle unit;
a piezoelectric element which comes into contact with the movable plate at one end of the piezoelectric element in an expansion or contraction direction to deform the movable plate; and
a support member which comes into contact with the piezoelectric element at other end of the piezoelectric element in the expansion or contraction direction,
wherein at least one of a contact portion of the movable plate and the piezoelectric element and a contact portion of the piezoelectric element and the support member is adhered by a hard material containing adhesive in which a hard material with a larger elastic modulus than a hardened adhesive is mixed.

* * * * *